United States Patent [19]

Mamajek et al.

[11] 4,207,890
[45] Jun. 17, 1980

[54] DRUG-DISPENSING DEVICE AND METHOD

[75] Inventors: Ronald C. Mamajek, Glenside, Pa.; Ernest S. Moyer, Grafton, W. Va.

[73] Assignee: McNeilab, Inc., Fort Washington, Pa.

[21] Appl. No.: 944,518

[22] Filed: Sep. 21, 1978

Related U.S. Application Data

[63] Continuation-in-part of Ser. No. 756,654, Jan. 4, 1977.

[51] Int. Cl.² ............................................. A61D 7/00
[52] U.S. Cl. .................................... 128/223; 128/260
[58] Field of Search .............................. 128/222-223, 128/260-261; 424/14, 19, 31-32, 36

[56] References Cited

U.S. PATENT DOCUMENTS

| | | | |
|---|---|---|---|
| 3,247,066 | 4/1966 | Milosovich, Jr. | 424/19 |
| 3,732,865 | 5/1973 | Higuchi et al. | 128/260 |
| 3,760,805 | 9/1973 | Higuchi | 128/260 |
| 3,828,777 | 8/1974 | Ness | 128/260 |
| 3,845,770 | 11/1974 | Theeuwes et al. | 128/260 |
| 3,901,232 | 8/1975 | Michaels et al. | 128/260 |
| 3,916,899 | 11/1975 | Theeuwes et al. | 128/260 |
| 3,929,132 | 12/1975 | Higuchi | 128/260 |
| 3,944,064 | 3/1976 | Bashaw et al. | 128/260 |
| 3,952,741 | 4/1976 | Baker | 128/260 |
| 3,976,764 | 8/1976 | Watanabe et al. | 424/19 |
| 3,977,404 | 8/1976 | Theeuwes | 128/260 |
| 3,987,790 | 10/1976 | Eckenhoff et al. | 128/260 |
| 3,991,759 | 11/1976 | Urquhart | 128/260 |
| 3,995,631 | 12/1976 | Higuchi et al. | 128/260 |
| 4,007,258 | 2/1977 | Cohen et al. | 424/36 |
| 4,016,880 | 4/1977 | Theeuwees et al. | 128/260 |
| 4,034,758 | 7/1977 | Theeuwes | 128/260 |

FOREIGN PATENT DOCUMENTS 2328580 1/1974 Fed. Rep. of Germany .

Primary Examiner—Robert W. Michell
Assistant Examiner—C. F. Rosenbaum
Attorney, Agent, or Firm—Geoffrey G. Dellenbaugh

[57] ABSTRACT

A drug-dispensing device and method for controlled and prolonged internal administration of medicaments to warm-blooded animals comprising an outer polymer envelope containing an expanding agent, drug metering means, and the drug itself. The outer polymer envelope is permeable to both the drug and body fluids and expands when the expanding agent is contacted by body fluids when the device is in the environment of use (e.g., the stomach). This expansion maintains the device in the environment of use while the drug is administered by the metering means.

9 Claims, 6 Drawing Figures

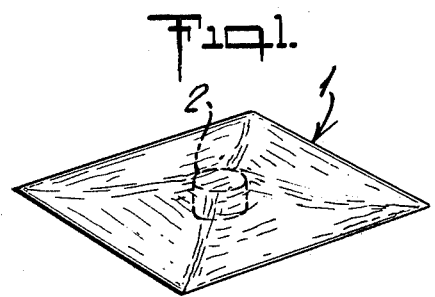
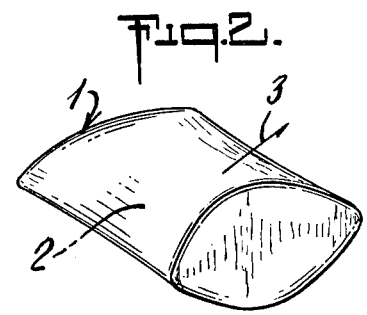
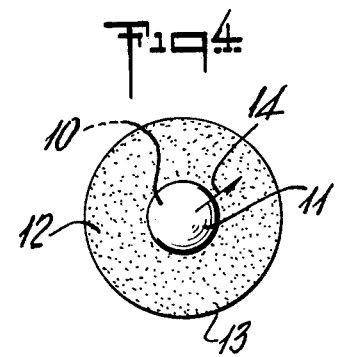
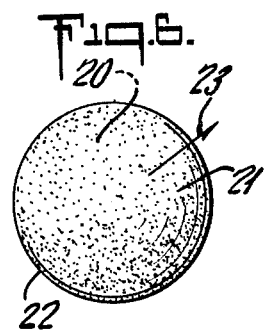

DRUG-DISPENSING DEVICE AND METHOD

RELATED APPLICATION

This application is a continuation-in-part of our co-pending application Ser. No. 756,654, filed Jan. 4, 1977.

BACKGROUND OF THE INVENTION

The present invention relates to devices for administering drugs, and more particularly to devices for the prolonged internal administration of drugs to warm-blooded animals.

The medical profession has long sought devices whereby drugs could be internally administered to warm-blooded animals in a controlled fashion over prolonged intervals. As an approximation to this sought after controlled, prolonged administration, it is the common practice today to administer drugs in oral doses at fixed periods of time. This practice results in a large amount of the drug being in the patient's blood stream shortly after administration of the dose, with the concentration decreasing thereafter. If it is desired to maintain a certain minimum level of the drug in the blood stream at all times, then amounts far in excess of this minimum level must be tolerated just after the dose is administered so that the minimum amount will be present just before the next dose is administered. While this procedure is recognized to be less than desirable, it has long been followed as the method of choice.

Even so-called "sustained release," "timed release," "prolonged release" or "controlled release" dosage forms merely extend the time period over which a drug is released, without prolonging the retention of the dosage form in the environment of use. Thus, a "timed release" oral capsule provides drug release for only as long as the capsule or its contents are retained in the gastrointestinal tract without prolonging this period of retention. The retention time (dwell time) of a dosage form in, for example, the gastrointestinal tract, varies from species to species, from individual to invididual, and for the same individual under different conditions. The retention time of conventional "timed release" dosage forms in the gastrointestinal tract is about 8-12 hours.

Many prior art devices exist for the dispensing of drugs within an animal body. These devices generally fall into one of the following categories.

First, there are devices illustrated by Higuchi U.S. Pat. Nos. 3,732,865; 3,760,805; 3,929,132; and 3,995,631; and Eckenhoff U.S. Pat. No. 3,987,790. These devices generally comprise a rigid outer shell within which are two chambers, one of which chambers is impervious to body fluid and contains drug and the other of which is permeable to body fluids and contains an osmotically effective solute. Body fluid flows by osmosis into the second compartment, thereby exerting pressure upon the first compartment and forcing drug out through a hole therein.

While these "osmotic pump" devices are useful for the controlled administration of drug, they are not retained in the stomach for any longer time than a conventional capsule and hence do not provide administration of drug for a period longer than about 8 to 12 hours.

A second group of devices is exemplified by the following U.S. Patents, all assigned to Alza Corporation: Nos. 3,828,777; 3,845,770; 3,916,899; 3,977,404; 3,991,759; 4,016,880; and 4,034,758. These devices generally comprise a rigid wall surrounding a drug composition, the wall being permeable to an external fluid but substantially impermeable to the drug composition contained therein. There is a passageway in the wall through which the drug solution is expelled due to the osmotic pressure generated within the device by the flow of fluid through the wall. These devices are generally taught to be used in the eye, although other locations (including orally) are also mentioned. It is clear that these devices would not be retained in the stomach for any longer than a conventional capsule and would be expelled within about 8 to 12 hours.

Baker U.S. Pat. No. 3,952,741, relates to a device comprising a semi-permeable wall surrounding a drug composition, which wall is permeable to water but not to the drug contained therein. When the osmotic pressure inside the device is sufficiently great due to the flow of water thereinto, the wall ruptures and the drug is dispensed all at once. This device does not provide a controlled, prolonged dispensing of drug. Moreover, once the device has burst it will not be retained within the stomach any longer than the usual residence time; i.e., about 8 to 12 hours.

Recently, however, there has been work toward the development of a device which would be retained in the environment of use (e.g., the stomach) and would dispense the drug in a controlled fashion over a long period of time, i.e., in excess of twelve hours.

Such a device is illustrated by U.S. Pat. Nos. 3,901,232 and 3,944,064. This device comprises a collapsed support, on the outside of which is attached a means for dispensing drug and inside of which is a material that is solid or liquid at room temperature but becomes a gas at body temperature. When this device is swallowed, the material inside the support is converted into a gas and expands the support, thereby retaining the device within the stomach. While these devices are retained within the stomach for longer than the usual residence time, they suffer from several disadvantages. They require a number of assembling steps and thus are considerably more difficult to make than the conventional capsule or tablet. Moreover, the use of the easily vaporized material to inflate the collapsed support may have unwanted side effects when this vaporizable material is released from the device within the body.

Another example of such a device is that described in German Pat. No. 2,328,580 to Banker, which discloses and claims a device comprising a drug-containing core coated with a hydratable polymeric film. The film material swells due to hydration when in contact with gastric juice to a size sufficient to retain the device in the stomach.

However, prior art devices have various disadvantages, such as not being retained in the environment of use for a sufficient period of time, not providing a longer duration of drug action than conventional dosage forms, being difficult to manufacture, and the like.

The device of the present invention is designed to overcome these disadvantages of the prior art and to provide a means whereby prolonged internal administration of medicaments at a controlled rate is possible.

SUMMARY OF THE INVENTION

There is provided by the present invention a drug dispensing device for controlled and prolonged internal (e.g., oral) administration of a drug to warm-blooded animals which comprises a collapsed, expandable, imperforate polymer envelope containing within it an effective expanding amount of an expanding agent, and drug metering means containing the drug and retained by this polymer envelope. In its collapsed state the device is of a size adapted to pass into the environment of use (e.g., down the esophagus and into the stomach). The phrase "retained by this polymer envelope" is intended to indicate that the drug metering means may be contained within the polymer envelope or may be the polymer envelope itself acting as a permeable membrane. The latter is preferred. The term "imperforate" as used herein means that the polymer envelope has no gross openings or apertures, while still being permeable to both drug and body fluids as discussed below. This polymer envelope is substantially non-hydratable but is permeable to both the drug and body fluids and expands when the expanding agent inside the polymer envelope is contacted by body fluids. The phrase "effective expanding amount" of expanding agent means an amount which (in combination with the drug) is sufficient to cause the polymer envelope to expand to the desired predetermined volume. Since the osmotic pressure of the drug will vary with the identity thereof, the effective expanding amount of the expanding agent will also vary with the drug used, all other factors being constant. This effective expanding amount can thus vary over a large range and can even be zero for a highly soluble, low potency drug. This expanded polymer envelope has a volume sufficient to cause retention of the device in the environment of use (e.g., the stomach) while the drug metering means effects a controlled and prolonged release of the drug. Since the entire purpose of the subject device would be frustrated if the polymer envelope were to burst due to the pressure within it caused by the expanding agent, it should be understood that the envelope must be sufficiently strong to withstand this pressure without bursting.

The drug dispensing device of the invention may be administered, for example, orally for systemic or local application of the drug contained therein. When the device is in the environment of use, body fluid flowing through the polymer envelope will contact the expanding agent and will cause the volume of the device to increase, thereby retaining it in the environment of use for at least the minimum desired time while the drug is released at a rate controlled by the drug metering means. After the drug has been released, the device will be expelled by the body. Factors contributing to this expulsion are a decrease in its volume or rigidity (e.g., due to escape of drug or expanding agent), the biodegradation of bioerosion of the polymer envelope, the orientation of the polymer envelope with respect to the pyloric sphincter (in the gastrointestinal tract), and the like. The phrase "the minimum desired time" as used herein means a time period longer than achieved by conventional dosage forms; i.e., at least eight hours and preferably at least twelve hours. This time period may differ for different drugs and can readily be determined by one skilled in the pharmaceutical art.

The polymer envelope may be made of an elastic material such as, for example, styrene-butadiene block copolymers sold by Shell Chemical Company under the name "Kraton," polyurethane materials sold by B. F. Goodrich Chemical Company under the name "Estane," and the like, in which case the expanding agent will cause it to distend like a balloon being inflated with air. The polymer envelope may also be made of a substantially non-elastic material such as, for example, collagen, microporous polyethylene, a polyamide such as nylon 4, nylon 818 or the like, polyvinyl acetate, microporous polypropylene, ethylene vinyl acetate copolymer, or the like, in which case the expanding agent will cause the polymer envelope to occupy its maximum volume without causing any distension thereof. The permeability of the polymer envelope to the drug and to body fluids may be an inherent characteristic of the material from which it is made (e.g., polyamides or polyvinyl acetate) or may be produced by forming the polymer envelope from a non-permeable material having minute quantities of a body fluid soluble material admixed therein (e.g., an elastic material impregnated with a soluble pharmaceutically acceptable, non-toxic salt such as magnesium sulfate or sodium chloride or a swellable resin as described below.) It is contemplated that any permeable polymer may be used which is insoluble and substantially non-hydratable in body fluids in the contemplated period of use; i.e., up to about ten days.

The expanding agent may be any pharmaceutically acceptable non-toxic material which causes osmotic pressure within the polymer envelope such as a body fluid soluble, non-toxic compound such as, for example, a sugar or sugar derivative such as sucrose, fructose, dextrose, lactose, mannitol, and the like, a salt such as magnesium sulfate, sodium chloride, and the like, or other suitable compounds. When the drug being dispensed by the subject device is a highly soluble, low potency drug such as, for example, lithium carbonate, calcium lactate, potassium iodide, potassium chloride, and the like, little or no expanding agent will generally be needed. If a high-potency drug is being dispensed, an additional expanding agent will generally be required. Such osmotic expanding agents are preferred if the polymer envelope is made of a substantially non-elastic material.

The expanding agent may also be a material which swells in volume when contacted by body fluids such as, for example, swellable resins or hydrocolloids. Suitable resins are those sold by Rohm and Haas Company under the registered trademark "Amberlite." Amberlite IR-116 (a styrene-divinylbenzene copolymer) has been found to be particularly useful. Suitable hydrocolloids include celluloses such as the crosslinked carboxymethylcellulose sold by Hercules Chemical Company under the name "Aqualon," collagens, and the like. Such swellable expanding agents are preferred if the polymer envelope is made of an elastic material.

The drug metering means is preferably the outer polymer envelope itself acting as a permeable membrane, but may also in some cases be a second permeable envelope contained within this outer envelope. The polymer envelope must in any case be designed so that its expanded volume is sufficient to retain the device in the environment of use over a prolonged period for the particular predetermined size and species of warm-blooded animals for which it is designed.

While the efficacy of the device both to dispense drug in a controlled fashion and to be retained in the environment of use (e.g., stomach) has been illustrated by experiments in dogs, it is contemplated that the device of the invention can be used on any size and species of warm-blooded animals, including humans, and that only a minimum amount of testing is required to determine the dimensions of the device which are necessary to cause it to be retained in the intended environment of use for the desired period of time.

The drug dispensing devices of the invention are generally prepared as follows. A sheet of the polymer from which the first envelope is to be fabricated is prepared to predetermined dimensions by known techniques, such as solution casting, thermal casting or the like. The sheet is folded and sealed along two sides to make a packet with one open end. Into the packet are inserted the drug and (if desired) the additional expanding agent, after which the open end of the packet is sealed. The sealing may be done by conventional techniques such as heat sealing, solution sealing, and the like.

For convenience in handling and dispensing and for subsequent administration, the resulting drug-containing packet may be inserted into a capsule or otherwise packaged, if desired.

If the polymer envelope is made of an elastic material, it may also be applied by spray coating a solution of said polymer onto a drug- and expanding agent-containing tablet in a Wurster-type spray coater. See U.S. Pat. Nos. 2,648,609 and 2,797,241 for a discussion of this spray coating technique. This spray coating method is in addition to the solution casting method discussed above.

If the elastic material is to contain a body fluid soluble material admixed therein, this latter material may be suspended in the polymer solution for either spray coating or solution casting as described above. The body fluid soluble material (e.g., inorganic salt) is milled to the desired size and homogeneously mixed in the polymer solution. The solvent used to make such solutions should be chosen so that the body fluid soluble material is insoluble therein to provide a dispersion of discrete particles thereof in the resulting polymer.

If the polymer envelope is made of a substantially non-elastic material, solution casting or thermal casting may be employed.

In view of the utility of the drug dispensing device of the invention, there is also provided a method for controlled and prolonged internal administration of a drug to a predetermined size and species of warm-blooded animal, including humans, which comprises internal administration of the subject device.

BRIEF DESCRIPTION OF DRAWINGS

FIG. 1 is a perspective view of an unexpanded or collapsed form of one embodiment of the drug delivery device of the invention.

FIG. 2 is a perspective view of the expanded device of FIG. 1.

FIG. 3 is a side view of the collapsed form of a second embodiment of the invention.

FIG. 4 is a side view of the expanded form of the device of FIG. 3.

FIG. 5 is a side view of the collapsed form of a variant of the second embodiment of the invention.

FIG. 6 is a side view of the expanded form of the device of FIG. 5.

DETAILED DESCRIPTION OF THE DRAWINGS

The drawings described briefly above illustrate three specific examples of drug delivery devices of the invention, which examples are not to be construed as limiting.

Referring to FIG. 1, there is shown a collapsed outer polymer envelope 1 which encloses a tablet 2 comprising drug and expanding agent. The volume of the drug and expanding agent tablet 2 is substantially smaller than the volume of outer polymer envelope 1. Referring to FIG. 2, the same device is shown in its expanded state in the environment of use. The outer polymer envelope 1 has expanded due to the osmotic pressure caused by the solution of the drug and expanding agent within it indicated generally by numeral 2. Drug is being dispensed through polymer envelope 1 as indicated by the arrow designated numeral 3. The example of the device illustrated by FIGS. 1 and 2 is generally referred to in this specification as the "first preferred embodiment".

Referring now to FIG. 3, there is shown the collapsed state of a device of the invention wherein the outer polymer envelope is of the elastic sort. Specifically, the delivery device is shown to comprise a drug mixture 10, surrounded by a first polymer envelope 11 for metering the drug, which in turn is surrounded by expanding agent 12 which swells when contacted with body fluids, the whole being surrounded by elastic polymer envelope 13. Referring to FIG. 4, the device of FIG. 3 is shown in an expanded state in the environment of use. Outer polymer envelope 13 has expanded due to the pressure of the swellable expanding agent 12 within it. Drug solution indicated by numeral 10 is contained within inner polymer envelope 11 acting to meter the exit of the drug as illustrated by the arrow designated numeral 14. This example of the device of the invention is hereinafter referred to as the "second preferred embodiment".

Referring to FIGS. 5 and 6, there is seen a variant of this second preferred embodiment in which the metering means is the outer polymer envelope itself and no second polymer envelope is present. Thus, drug mixture 20 is surrounded by a swellable expanding agent 21 and the whole enclosed by elastic outer polymer envelope 22. This is shown in FIG. 5 in the collapsed state, while in FIG. 6, the elastic polymer envelope 22 has expanded due to the pressure of the expanding agent 21 within it. Drug is being dispensed from the device through the elastic polymer envelope as indicated by the arrow designated 23.

DESCRIPTION OF THE PREFERRED EMBODIMENTS

A. First Preferred Embodiment

In one preferred embodiment of the present invention, the polymer envelope, which also comprises the drug metering means, is made of a substantially non-elastic, imperforate, substantially non-hydratable material which is inherently permeable to both the drug being used and body fluids, such as a polyamide. In this preferred embodiment, the expansion of the envelope is caused by osmotic pressure generated by either the drug itself if the drug has sufficient solubility in body fluids or by the drug plus an additional expanding agent inducer such as those discussed above if the drug is not sufficiently soluble. The solid volume of the drug (and additional expanding agent, if present) is substantially smaller (i.e., less than about 75% and preferably less than about 50%) than the maximum volume of the polymer envelope. When this embodiment (in its collapsed form) is placed in the environment of use (e.g., the stomach), body fluid flowing through the polymer envelope causes it to attain its maximum volume because of the presence of the drug (and expanding agent) and thus be retained in the environment of use. The drug then flows through the polymer envelope at a rate controlled by the composition of said envelope.

B. Second Preferred Embodiment

In a second preferred embodiment of the present invention, the polymer envelope is made of an elastic, imperforate, substantially non-hydratable material such as any of the polyurethane materials sold by B. F. Goodrich Chemical Company under the registered trademark "Estane," any of the styrene-butadiene block copolymers sold by Shell Chemical Company under the registered trademark, "Kraton," or the like, to which a body-fluid soluble material such as magnesium sulfate, sodium chloride, or the like has been admixed in minute particles to make the polymer envelope permeable to drug and body fluids. The salt dissolves in the presence of body fluids, making the resulting polymer permeable to body fluids and drug. The material designated as "Estane 5701-F1," which has a specific gravity of 1.20, a tensile strength of 5,500 psi, and a Brookfield viscosity of 300–700 cps (15% TS in tetrahydrofuran, No. 2 spindle, 20 rmp, 25° C.), has been found to work well. Contained inside this polymer envelope is an expanding agent which swells in reaction to being contacted with body fluids, so that the polymer envelope is caused to expand upon contact with body fluids in the environment of use. Also contained within the polymer envelope is the drug, which is dispensed at a controlled and predetermined rate based upon the permeability of the envelope. As an alternate embodiment there may be a reservoir of drug enclosed within an inner second polymer envelope, all contained within the outer polymer envelope, which inner polymer envelope acts as the drug metering means. The outer polymer envelope in this version of the second preferred embodiment is designed with a permeability sufficiently greater than that of the inner second polymer envelope so as not to interfere with the diffusion of the drug as controlled by said inner second polymer envelope. In both of these variations, the osmotic pressure contributed by the drug assists in the expansion of the outer polymer envelope.

Those skilled in the art can readily determine the rate of diffusion of drugs through materials and select suitable combinations of polymer envelope and drug for particular applications. Various techniques can be used to determine the permeability of materials to different drugs. One that has been found to be well suited is to prepare a film of the material by thermal or solution casting to a thickness in the range of 0.1 to 60 mils. The film is used as a barrier between a homogeneous saturated solution of the drug and a rapidly stirred solvent bath, both maintained at constant temperature (typically 37° C.). Samples are periodically withdrawn from the solvent bath and analyzed for drug concentration. By plotting drug concentration in the solvent bath versus time, the permeability constant P of the film in square centimeters/time is determined by Fick's first law of diffusion.

$$\text{Slope of plot} = \frac{Q_1 - Q_2}{t_1 - t_2} = P \frac{AC}{h}$$

wherein:
  $Q_1$ equals cumulative amount of drug in solvent in micrograms at $t_1$;
  $Q_2$ equals cumulative amount of drug in solvent in micrograms at $t_2$;
  $t_1$ equals elasped time to first sample (i.e., $Q_1$);
  $t_2$ equals elasped time to second sample (i.e., $Q_2$);
  A equals area of membrane in square centimeters;
  C equals concentration of drug at saturation in mg/cc; and
  h equals thickness of membrane in centimeters.

By determining the slope of the plot and solving the equation using the known or measured value of A, C, and h, the permeability constant P of the film for a given drug is readily determined. Of course, this permeability constant is an inherent characteristic of the film for a particular drug, diffusion medium, and temperature and is unchanged whether the material is used as the outer polymer envelope or the inner drug metering means.

For a particular drug and polymer envelope material, the rate at which drug is dispensed from a packet can be controlled by varying the area or thickness of the polymer envelope. This area can be controlled either by changing the dimensions of the polymer envelope or by incorporating into the envelope a nonpermeable section. This nonpermeable section would reduce the area to be considered in the above discussion and would thus decrease the rate at which the drug is dispensed from the device. This nonpermeable section can be achieved by coating a portion of the polymer envelope with a solution of a nonpermeable polymer (e.g., collodion or polyvinyl butyral in ethanol) and allowing it to dry.

The rate at which drug is dispensed from a packet may also be controlled by varying the size of the microporous openings. If the mean diameter of the microporous openings is significantly smaller than the minimum dimension of the drug molecule (while still being larger than the minimum dimension of a water molecule), essentially no drug will be dispensed through the openings, and the film is described as being "semiporous". Such semiporous films are not useful for preparation of the present invention, since the film must be permeable to the drug. Routine testing of microporous polymer films will determine what combination of pore diameter and thickness is preferred for a particular drug.

It is contemplated that any drug which is soluble in body fluids and which is suitable for administration orally, rectally, or the like, could be used in the device of the invention. Good results have been obtained with poldine methylsulfate, propoxyphene hydrochloride, and haloperidol. These drugs are of varying solubility in stomach fluid, the first being very soluble at all pH values, the second being very soluble at acid pH, and the third having low solubility at all pH values.

The present invention is illustrated by the following examples.

EXAMPLE I

This example demonstrates P determination of a collagen film (DEVRO brand sausage casing; product code 74-235) manufactured by DEVRO, Inc. in 0.1 N HCl at 25° C. for two drugs according to the procedure described above.

| A. Poldine methyl sulfate | Slope = 9.60 mg/hr |
|---|---|
| | Slope = $P \frac{AC}{h}$ |
| | $9.60 = \frac{P(1.27)(1670)}{.0036}$ |
| | $P = 1.63 \times 10^{-5}$ cm$^2$/hr |
| B. Haloperidol | Slope = .045 mg/hr |
| | Slope = $P \frac{AC}{h}$ |
| | $.045 = \frac{P(1.27)(.43)}{.0031}$ |
| | $P = 2.56 \times 10^{-4}$ cm$^2$/hr |

EXAMPLE II

The retention of several devices of the invention in the gastrointestinal tract of dogs was determined in beagles by administration through a gastric fistula and by oral administration of packets containing barium sulfate and monitoring the residence time thereof by X-ray, or by observation in stools or upon sacrifice of the animal. The results are presented in the following table, which gives the material used in the packet, the flat dimensions of the packet, and the retention results.

The polyethylene packets were made by heat sealing commercially-available polyethylene film having a thickness of 2 mil. The nylon 4 and nylon 4/resin packets were made by casting the polymer film to a thickness of 1–3 mils from a solution in formic acid and solution sealing with the same solvent. The Amberlite IRP 88 and Amberlite IRP 58 resins used were 100–400 mesh.

TABLE

| Packet Material | Flat Dimensions (cm) | Location and time after Administration (hrs) | | |
|---|---|---|---|---|
| | | Stomach | Intestinal Tract | Stools |
| Polyethylene | 1.5 × 3.0 | | 16 | 22 |
| Polyethylene | 1.5 × 4.0 | 94 | | |
| Polyethylene | 1.0 × 4.5 | 48 | 70 | 96 |
| Polyethylene | 1.0 × 1.0 | | 8 | 29 |
| Nylon 4 | 1 × 2 | | 16 | 22 |
| Nylon 4 | 1 × 2 | | 17 | 22 |
| Nylon 4 | 2 × 4 | 72 | | 94 |
| Nylon 4 | 2 × 4 | 72 | 95 | 120 |
| Nylon 4/IRP 88* | 1 × 2 | 17 | | 40 |
| Nylon 4/IRP 88* | 1 × 2 | | 17 | 22 |
| Nylon 4/IRP 88* | 2 × 4 | 16 | | 45 |
| Nylon 4/IRP 88* | 2 × 4 | 65 | 88 | 140 |
| Nylon 4/IRP 58* | 2 × 4 | 88 | | 93 |
| Nylon 4/IRP 58* | 2 × 4 | 264 | | |

*90/10 Nylon 4/resin on a wt/wt basis.

EXAMPLE III

Following the procedure of Example II, packets of ESTANE 5701 polyurethane admixed with 10% by weight of the indicated soluble salt of Amberlite ion exchange resin were administered to beagles to measure residence time in the gastrointestinal tract. The packets were prepared from solution cast polymer (tetrahydrofuran as solvent) and thermally sealed. The MgSO$_4$ was 200 mesh and the IRP 88 was 100–400 mesh. The results are given in the following table.

TABLE

| Packet Material | Flat Dimensions (cm) | Location and time after Administration (hrs) | |
|---|---|---|---|
| | | Stomach | Stools |
| ESTANE 5701/MgSO$_4$ | 1.0 × 3.0 | 17 | 23 |
| ESTANE 5701/MgSO$_4$ | 1.0 × 3.25 | >24 | 112 |
| ESTANE 5701/MgSO$_4$ | 1.0 × 3.5 | >17 | 90 |
| ESTANE 5701/MgSO$_4$ | 1.0 × 3.75 | >23 | 46.5 |
| ESTANE 5701/MgSO$_4$ | 1.0 × 4.0 | 25 | 49 |
| ESTANE 5701/MgSO$_4$ | 1.5 × 3.0 | >72.5 | 123.5 |
| ESTANE 5701/MgSO$_4$ | 1.5 × 3.25 | 49 | 72 |
| ESTANE 5701/MgSO$_4$ | 1.5 × 3.75 | >7 but <26 | 49 |
| ESTANE 5702/MgSO$_4$ | 1.5 × 4.0 | >18 but <23 | 41 |
| ESTANE 5701/MgSO$_4$ | 2.0 × 3.5 | 19 | 44 |
| ESTANE 5701/IRP88 | 1.0 × 3.0 | <17.5 | 41.5 |
| ESTANE 5701/IRP88 | 1.0 × 3.25 | 17.24 | 41.5 |
| ESTANE 5701/IRP88 | 1.0 × 3.5 | <17.5 | 41.5 |
| ESTANE 5701/IRP88 | 1.5 × 3.25 | 18 | 48 |
| ESTANE 5701/IRP88 | 1.5 × 3.5 | <18 | 40.5 |
| ESTANE 5701/IRP88 | 1.5 × 3.75 | <18 | 40.5 |
| ESTANE 5701/IRP88 | 1.5 × 4.0 | 18 | 40.5 |
| ESTANE 5701/IRP88 | 2.0 × 3.0 | <18.5 | 40.5 |
| ESTANE 5701/IRP88 | 2.0 × 3.25 | 18.5 | 40.5 |
| ESTANE 5701/IRP88 | 2.0 × 3.5 | >42.5 | 64.5 |
| ESTANE 5701/IRP58 | 1.0 × 3.0 | >17.3 | 41.5 |
| ESTANE 5701/IRP58 | 1.0 × 3.25 | <17.4 | 41.5 |
| ESTANE 5701/IRP58 | 1.0 × 3.75 | <18 | 22.5 |
| ESTANE 5701/IRP58 | 1.0 × 4.0 | <18 | 22.5 |
| ESTANE 5701/IRP58 | 1.5 × 3.0 | 17 | 41 |
| ESTANE 5701/IRP58 | 1.5 × 3.25 | 24 | 41 |
| ESTANE 5701/IRP58 | 1.5 × 3.75 | 41 | 65 |

EXAMPLE IV

Following the procedure of Example III, packets were made of ESTANE 5701 polyurethane admixed with 10% by weight of 200–270 mesh sodium chloride and containing Amberlite IR-116 swellable ion exchange resin. These products were administered to beagles as in Example II to measure residence time in the gastrointestinal tract. The results are given in the following table.

TABLE

| Flat Packet Dimensions (cms) | Location and time after Administration (hrs) | |
|---|---|---|
| | Stomach | Stools |
| 1.5 × 3.5 | 23.5 | 64.5 |
| 1.6 × 3.3 | — | 41 |
| 1.6 × 3.5 | 40 | 65 |
| 1.6 × 3.7 | 24 | 41 |
| 1.6 × 3.7 | — | 19 |
| 1.6 × 3.7 | — | 17 |
| 1.7 × 3.2 | — | 16.5 |
| 1.7 × 3.5 | 24 | 45 |
| 1.7 × 3.7 | — | 17.5 |
| 1.7 × 3.7 | 24 | 44 |
| 1.8 × 3.2 | 24 | 41 |
| 1.8 × 3.3 | — | 19 |
| 1.8 × 3.5 | — | 16.5 |

EXAMPLE V

Barium sulfate tablets having a diameter of ½ inch were spray coated in a Wurster-type sprayer with a solution of ESTANE 5701 in tetrahydrofuran containing 10% by weight of 200 mesh MgSO$_4$. These tablets were found in dog stomachs upon sacrifice at 24 hours and 48 hours after oral administration thereof.

EXAMPLE VI

The ability of nylon packets to dispense poldine methylsulfate was determined by administering packets to beagles, maintaining them in the stomach, and then monitoring the elevation of the dogs' heart rate. The packets of nylon 818 were solution cast from methanol and thermally sealed, while the packets of nylon 4 were solution cast from formic acid and solution sealed with the same solvent. The packets had thicknesses of 1–10 mils.

First, baselines and dose response curves were established. Then a packet containing poldine methylsulfate was administered intragastrically, kept in the stomach by means of a string through the gastric fistula, and the dog's heart rate monitored as a function of time. The observed duration of the poldine activity for each packet is given in the following table. For comparison, administration of the same amount of drug in a single conventional bolus dose would result in a duration of activity for less than twenty hours. The utility of the tested packets to dispense drug over a prolonged time interval when maintained in the stomach is thus demonstrated.

TABLE

| Packet Composition | Flat Dimensions (cm) | Observed Duration (hrs) |
| --- | --- | --- |
| Nylon 818 | 1.35 × 1.8 | >24 |
| Nylon 818 | 1.3 × 1.8 | 23 |
| Nylon 818 | 1.1 × 2.4 | 33 |
| Nylon 818 | 0.9 × 2.9 | 30 |
| Nylon 818 | 1.3 × 1.5 | 42 |
| Nylon 4 | 1.2 × 2.0 | >28 |
| Nylon 4 | 1.1 × 1.3 | >36 |
| Nylon 4 | 0.95 × 1.05 | 42 |
| Nylon 4 | 1.0 × 3.0 | 26 |
| Nylon 4 | 1.0 × 2.5 | 24 |
| Nylon 4 | 1.0 × 1.5 | 40 |
| Nylon 4 | 1.3 × 1.5 | 26 |
| Nylon 4 | 1.5 × 2.5 | 41 |

EXAMPLE VII

The duration of in vivo activity of a packet containing haloperidol was determined by orally administering the packet to a beagle and monitoring the activity of the haloperidol to antagonize apomorphine induced emesis. The packet had flat dimensions of 1.1×2.6 cm and was made of one mil microporous polypropylene sold by Celanese Company under the registered trademark "Celgard." The dog was challenged daily by subcutaneous administration of an emetic dose of apomorphine until three successive days of emesis occurred, and the duration of activity was measured to the first day of this period. Duration of activity for this packet was nine days, as compared to five days when the same dose was administered in a conventional dosage form.

These examples demonstrate the utility of the drug dispensing device of the invention. Devices of greater size than about 1×1.5 cm are retained for prolonged periods in beagles. Examples VI and VII show that prolonged controlled administration of drugs can be obtained in beagles using the device of the invention having dimensions greater than about 1×1.5 cm. It is contemplated that similar prolonged controlled administration of drugs can be achieved in any size and species of warm-blooded animal with the device of the invention.

The above examples have been given only by way of illustration and not to limit the scope of the present invention, which scope is defined in the following claims.

What is claimed is:

1. A drug dispensing device for controlled and prolonged internal administration of a drug to a predetermined size and species of warm-blooded animal which comprises:
   (a) a collapsed, expandable, imperforate envelope made of a substantially non-hydratable, body fluid permeable, drug-permeable polymer film;
   (b) drug metering means containing said drug and retained by said polymer envelope, whereby drug is dispensed at a predetermined rate; and
   (c) an effective expanding amount of an expanding agent contained within said polymer envelope, the combination of which agent and which drug when in contact with body fluids cause said polymer envelope to expand to a volume such that the device is retained in the environment of use for at least the minimum desired time.

2. The drug dispensing device of claim 1 wherein said drug metering means is the polymer envelope itself acting as a drug-permeable membrane.

3. The drug dispensing device of claim 2 wherein the polymer envelope is made of a member selected from the group consisting of collagen, microporous polyethylene, a polyamide, a polyurethane, a styrene-butadiene block copolymer, polyvinyl acetate, microporous polypropylene, and ethylene vinyl acetate copolymer.

4. A drug dispensing device for controlled and prolonged internal administration of a drug to a predetermined size and species of warm-blooded animal which comprises:
   (a) a collapsed, expandable, imperforate envelope made of a substantially non-hydratable, substantially non-elastic, body fluid permeable, drug-permeable polymer film; and
   (b) a drug contained within said polymer envelope, the volume of said drug being substantially smaller than the maximum volume of said polymer envelope, and the body fluid solubility of said drug and the drug permeability of said polymer envelope being so related that when said device is in the environment of use:
      (i) said polymer envelope is expanded by the osmotic pressure of said body fluids therein dissolving said drug; and
      (ii) said drug is dispensed by said device at a predetermined rate; the expanded volume of said polymer envelope being such that the expanded device is retained in the environment of use for at least the minimum desired time.

5. A drug dispensing device for controlled and prolonged internal administration of a drug to a predetermined size and species of warm-blooded animal which comprises:
   (a) a collapsed, expandable, imperforate envelope made of a substantially non-hydratable, substantially non-elastic, body fluid permeable, drug-permeable polymer film;
   (b) an effective expanding amount of an expanding agent contained within said polymer envelope, which agent dissolves when in contact with body fluids to cause (in combination with said drug) said polymer envelope to expand due to osmotic pressure to a volume such that the expanded device is retained in the environment of use for at least the minimum desired time; and
   (c) a drug contained within said polymer envelope, the combined volume of said drug and of said expanding agent being substantially smaller than the maximum volume of said polymer envelope, and the body fluid solubility of said drug and the drug permeability of said polymer envelope being so related that when said device is in the environment of use said drug is dispensed by said device at a predetermined rate.

6. A drug dispensing device for controlled and prolonged internal administration of a drug to a predetermined size and species of warm-blooded animal which comprises:
   (a) a collapsed, expandable, first imperforate envelope made of a substantially non-hydratable, elastic, body fluid permeable, drug-permeable polymer film;

(b) an effective expanding amount of an expanding agent contained within said first polymer envelope, which agent swells when in contact with body fluids to cause said first polymer envelope to expand to a volume such that the device is retained in the environment of use for at least the minimum desired time; and (c) a second imperforate envelope containing said drug and contained within said first polymer envelope, and made of a substantially non-hydratable, substantially non-elastic, body fluid permeable, drug-permeable polymer film, the drug permeability of said first polymer envelope being greater than the drug permeability of said second polymer envelope whereby drug is dispensed at a predetermined rate based on the permeability of said second polymer envelope.

7. A method for controlled and prolonged internal administration of a drug to a predetermined size and species of warm-blooded animal which comprises oral administration of a drug dispensing device comprising:
(a) a collapsed, expandable, imperforate envelope made of a substantially non-hydratable, body fluid permeable, drug-permeable polymer film;
(b) drug metering means containing said drug and retained by said polymer envelope whereby drug is dispensed at a predetermined rate; and
(c) an effective expanding amount of an expanding agent contained within said polymer envelope, the combination of which agent and which drug when in contact with body fluids cause said polymer envelope to expand to a volume such that the device is retained in the environment of use for at least the minimum desired time.

8. A method for controlled and prolonged internal administration of a drug to a predetermined size and species of warm-blooded animal which comprises oral administration of a drug dispensing device comprising:
(a) a collapsed, expandable, imperforate envelope made of a substantially non-hydratable, substantially non-elastic, body fluid permeable, drug permeable polymer film; and
(b) a drug contained within said polymer envelope, the volume of said drug being smaller than the maximum volume of said polymer envelope and the body fluid solubility of said drug and the drug permeability of said polymer envelope being so related that when said device is in the environment of use:
  (i) said polymer envelope is expanded by the osmotic pressure of said body fluids therein dissolving said drug; and
  (ii) said drug is dispensed by said device at a predetermined rate; the expanded volume of said polymer envelope being within a range such that the expanded device is retained in the environment of use for at least the minimum desired time.

9. A method for controlled and prolonged internal administration of a drug to a predetermined size and species of warm-blooded animal which comprises oral administration of a drug dispensing device comprising:
(a) a first collapsed, expandable, imperforate envelope made of a substantially non-hydratable, elastic, body fluid permeable, drug-permeable polymer film;
(b) an effective expanding amount of an expanding agent contained within said first polymer envelope, which agent swells when in contact with body fluids to cause said first polymer envelope to expand to a volume such that the device is retained in the environment of use for at least the minimum desired time; and
(c) a second imperforate envelope containing said drug and contained within said first polymer envelope, and made of a substantially non-hydratable, substantially non-elastic, body fluid permeable, drug-permeable polymer film, the drug permeability of said first polymer envelope being greater than the drug permeability of said second polymer envelope whereby drug is dispensed at a predetermined rate based on the permeability of said second polymer envelope.

* * * * *